United States Patent
Eibl

(10) Patent No.: US 9,326,989 B2
(45) Date of Patent: May 3, 2016

(54) OLEYL PHOSPHOCHOLINE

(75) Inventor: Hansjörg Eibl, Bovenden (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 1328 days.

(21) Appl. No.: 12/593,336

(22) PCT Filed: Mar. 26, 2008

(86) PCT No.: PCT/EP2008/002383
§ 371 (c)(1),
(2), (4) Date: Jan. 19, 2010

(87) PCT Pub. No.: WO2008/116641
PCT Pub. Date: Oct. 2, 2008

(65) Prior Publication Data
US 2010/0144676 A1 Jun. 10, 2010

(30) Foreign Application Priority Data
Mar. 26, 2007 (DE) .......................... 10 2007 014 375

(51) Int. Cl.
*A61K 31/685* (2006.01)
*A61K 45/06* (2006.01)

(52) U.S. Cl.
CPC .............. *A61K 31/685* (2013.01); *A61K 45/06* (2013.01)

(58) Field of Classification Search
CPC ............................ A61K 31/685; A61K 45/06
USPC ..................... 514/183, 77; 558/166
See application file for complete search history.

(56) References Cited

U.S. PATENT DOCUMENTS

| | | | |
|---|---|---|---|
| 5,290,769 A | 3/1994 | Eibl et al. | |
| 5,916,884 A | 6/1999 | Eibl et al. | |
| 8,828,972 B2 * | 9/2014 | Eibl et al. | 514/77 |
| 2007/0167408 A1 * | 7/2007 | Perrissoud et al. | 514/80 |

FOREIGN PATENT DOCUMENTS

| | | |
|---|---|---|
| DE | 198 35 611 A1 | 2/2000 |
| DE | 10 2004 055284 A1 | 5/2006 |
| EP | 0 534 445 A | 3/1993 |
| WO | 2007/071658 A | 6/2007 |

OTHER PUBLICATIONS

Unger et al. , In Vivo Antileishmanial Activity of Hexadecylphosphocholine and Other Alkylphophocholines, Drugs of Today 1998, 34 (Suppl. F): 133-140.*
Eibl et al. Alkylphosphocholines Inhibit Proliferation of Human Retinal Pigment Epithelial Cells, (IOVS, 2003, vol. 44, No. 8.*
Sundar et al., "Miltefosine in the treatment of leishmaniasis: Clinical evidence for informed clinical risk management", 2007, Therapeutics and Clinical Risk Management, 3(5), pp. 733-740.*
Unger C et al: "In Vivo Antileishmanial Activity of Hexadecylphosphocholine and Other Alkylphosphocholines" Drugs of Today / Medicamentos De Actualidad, J.R. Prous SS-A. International Publishers, ES, vol. 34, Jan. 1, 1998, pp. 133-140.
Seifert K et al: "Effects of Miltefosine and Other Alkylphosphochocines on Human Intestinal Parasite Entamoeba Histolytica" Antimicrobial Agents and Chemotherapy,American Society for Microbiology, Washington, DC, US, vol. 45, No. 5, May 1, 2001, pp. 1505-1510.
Eibl K H Et Al:"Oleyl—Phosphocholine Inhibits Proliferation of Human Rpe Cells" Investigative Ophthalmology & Visual Science, Association for Research in Vision and Ophthalmology, US, vol. 44, No. Suppl., Jan. 1, 2003, pp. 1-2.
Sobottka Stephan B et al: "Structure-activity relationships of four anti-cancer alkylphosphocholine derivatives in vitro and in vivo" International Journal of Cancer, John Wiley & Sons, Inc, United States, Switzerland, Germany, vol. 53, No. 3, Jan. 1, 1993, pp. 418-425.
Parfitt, "Martindale The complete drug reference", Jan. 1, 1997, Pharmaceutical Press, London, vol. 32, pp. 16-19, ISBN: 085369429X.

* cited by examiner

*Primary Examiner* — My-Chau T Tran
(74) *Attorney, Agent, or Firm* — Rothwell, Figg, Ernst & Manbeck, P.C.

(57) ABSTRACT

The invention relates to the use of oleyl phosphocholine and oleyl-phospho-(N.N.-dimethyl-N-ethyl)-ethyl-ammonium for the long-term and continuous treatment of serious illnesses, such as cancer, leishmaniasis, ehrlichiosis, multiple sclerosis and psoriasis, in addition to other indications mentioned in the application.

12 Claims, No Drawings

OLEYL PHOSPHOCHOLINE

CROSS REFERENCE TO RELATED APPLICATION

This application is a 35 U.S.C. 371 National Phase Entry Application from PCT/EP2008-002383, filed Mar. 26, 2008, which claims the benefit of German Patent Application No. 10 2007 014 375.5 filed on Mar. 26, 2007, the disclosure of which is incorporated herein in its entirety by reference.

The present invention relates to the use of oleyl phosphocholine for the long-term and continuous treatment of serious illnesses, such as for example cancer, parasitic diseases, bacterial infections, fungal diseases, multiple sclerosis and psoriasis. The antiproliferative properties of the alkyl phosphocholines, here in particular oleyl phosphocholine, are often important underlying factors in this action.

Parasitic diseases such as malaria and leishmaniasis are a major problem in third world countries, but are also increasing in western industrial countries. The causes of this are increasing tourism, and also dangers which have to be linked with global warming. In particular, leishmaniasis, a parasitic disease often having a fatal outcome, has become the focus of interest both in human medicine and also in veterinary medicine.

As described in EP 534 445, success in providing an effective oral therapy for the treatment of leishmaniasis was first achieved with hexadecyl phosphocholine.

Hexadecyl phosphocholine is a member of the alkyl phosphocholine class of substances with pronounced antiproliferative properties. Alkyl phosphocholines with active substance properties are chemically quite simple substances, namely phosphocholine esters of long-chain alcohols which contain 14 to 24 carbon atoms.

In principle, the alkyl phosphocholines with active substance properties against leishmaniasis, cancer, ehrlichiosis and psoriasis can be divided into two groups on the basis of the chain length of their alkyl chains. The first group contains alkyl chains with 16 to 20 carbon atoms, which owing to their lytic properties can only be used orally or topically. The side effects on subcutaneous administration are hemolysis, cytolysis, thrombophlebitis, etc. After oral administration, the alkyl phosphocholines concentrate in all body fluids and also in the tissues, but not in the heart. It is of great significance that the blood-brain barrier is permeable to alkyl phosphocholines. The brain takes up relatively large quantities of alkyl phosphocholines, without the occurrence of perceptible side effects. However, the shorter the alkyl chains are, the smaller the activity of the compounds becomes owing to the increased water solubility.

The second group comprises alkyl chains with 22 to 24 carbon atoms, which as alkyl phosphocholines can only be administered parenterally, since the absorption of these substances from the gastrointestinal tract is low (<10%). The molecules also pass through the blood-brain barrier and concentrate in the brain in considerable quantities.

The special position of hexadecyl phosphocholine ($C_{16}$-PC) within the homologous series of the alkyl compounds $C_{14}$-PC, $C_{16}$-PC and $C_{18}$-PC is surprising. Only hexadecyl phosphocholine has a usably good antitumor action, as can also be seen from the patent application EP 248 047 (animal experiments in rats). These results were also confirmed in protozoan diseases such as for example leishmaniasis. Again the special position of hexadecyl phosphocholine within the homologous series of alkyl phosphocholines becomes evident, as can also be seen from EP 534 445 (animal experiments in mice).

After the favorable results with hexadecyl phosphocholine in animal experiments, good results could also be achieved in the treatment of human leishmaniasis. The treatment with hexadecyl phosphocholine (brand names Miltefosin® or Impavido®) is effected with capsules (1.5 to 2.5 mg active substance per kg body weight per day) over a period of 28 days. Very common side effects are vomiting, diarrhea, nausea, increase in liver enzymes and increase in creatinine. Immuno-compromised patients should not be treated.

The unpleasant side effects with hexadecyl phosphocholine became particularly pronounced in the treatment of canine leishmaniasis. Canine leishmaniasis is a growing problem owing to the importation of dogs from southern countries. The activity of hexadecyl phosphocholine against canine leishmaniasis only started at 3 mg per kg body weight per day. Higher doses were not tolerated, and lower doses were almost ineffective. Thus a practical application of hexadecyl phosphocholine in animal health for the treatment of canine leishmaniasis was not effective owing to unpleasant side effects such as nausea, vomiting and a marked restriction of renal function under the conditions of the treatment. Also problematical were hemolytic and cytolytic properties, if oral administration was abandoned and subcutaneous or intravenous administration were used.

Said difficulties could then be overcome with the aid of liposome formulations. Through the incorporation of hexadecyl phosphocholine into liposome coats which were obtained by the addition of cholesterol, the hemolytic and cytolytic properties could be suppressed. The therapeutic action of hexadecyl phosphocholine was scarcely improved by the incorporation into liposomes. However, the side effects were markedly reduced.

A decisive improvement was only obtained by chemical structure variation. In a comparison of the therapeutic action of three alkyl phosphocholines of the same chain length, $C_{18}$-PC (octadecyl), $C_{18:1(trans)}$-PC (elaidyl) and $C_{18:1(cis)}$-PC (oleyl), in animal experiments, oleyl phosphocholine was found to be markedly superior to the other alkyl phosphocholines of the same chain length. It is particularly striking that the low toxicity in animal experiments leads to a large therapeutic index. In accordance with previous experience with hexadecyl phosphocholine and the favorable effect of liposomal formulations on compatibility observed there, oleyl phosphocholine was also used in liposomal form.

Among the different liposomal formulations with oleyl phosphocholine, DE 10 2004 055 284 should in particular be mentioned. This formulation consists of a simple lipid composition: oleyl phosphocholine, cholesterol and oleic acid, in a liposomal formulation, which can be sterile-filtered, heat-sterilized and stored at 4 to 8° C. for 3 years without problems. These oleyl phosphocholine liposomes can be easily produced. They are an important drug form for treating very refractory, chronic diseases in which oral administration may not be advisable because of disorders of the adsorption behavior in the gastrointestinal tract.

The cost pressure in our health service urgently necessitates the development of active substances and treatment forms which can cure or control serious diseases. As far as possible, these drugs should be made available to the patient and our health system at low cost. In these respects, a liposomal formulation is always disadvantageous.

The purpose of the present invention is therefore to provide a drug which on the one hand is easy to produce and inexpensive, but which on the other hand enables the treatment of serious diseases.

This purpose is achieved according to the invention by the use of compounds of the formula (I)

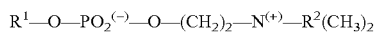

wherein
R$^1$ is an oleyl residue and
R$^2$ means CH$_3$ or CH$_2$CH$_3$,
for the production of a drug for the treatment of parasitic diseases, such as in particular leishmaniasis or malaria, cancer, multiple sclerosis, psoriasis, bacterial infections such as for example ehrlichiosis, and/or fungal diseases.

Surprisingly, it was found that compounds of the formula (I) and in particular oleyl phosphocholine on the one hand have decreased toxicity, and on the other are already active at very low dosages. This makes it possible to use these active substances as drugs without undesired side effects being observed. Furthermore, special formulations, for example liposome formulations, are no longer necessary. Hence according to the invention the compounds are preferably used in a non-liposomal form. On the contrary, simple oral administration of the active substance is possible and because of the low dosages required, no vomiting and no nausea occur in the patient. Furthermore, subcutaneous administration is also possible without irritation, again because of the small quantity of active substance required. Because of the high activity and the small active quantity required as a result, long-term and/or continuous treatments are also possible, in particular treatments over a period of more than 2 weeks, in particular of more than 4 weeks, but also of more than 2 months, in particular of more than 6 months.

After the favorable results with oleyl phosphocholine in liposomes in combination with the high therapeutic index observed with this, we surprisingly found that oleyl phosphocholine in therapeutically effective doses can also be used without liposomal packaging, in all dosage forms from oral to subcutaneous to intravenous. Surprisingly, at therapeutically effective dosages the side effects observed with hexadecyl phosphocholine do not occur. Even in long-term applications over several months, no deterioration in the renal values (increase in creatinine) is observed, quite the contrary: the renal values normalize very rapidly under the therapy. These results confirm the outstanding special position of oleyl phosphocholine in the alkyl phosphocholine series. Oleyl phosphocholine is the first alkyl phosphocholine which can be used orally and intravenously.

It is also of great significance for practical use that the stability of oleyl phosphocholine in injection or infusion solutions or also in the form of tablets can be guaranteed over a longer period even at 30° C. For use in veterinary medicine, it is also useful that mixtures of oleyl phosphocholine (90%) and hexadecyl phosphocholine (10%) can be used and can be made available extremely inexpensively from olive oil.

According to the invention, hexadecyl phosphocholine has been improved, and in particular the toxicity decreased, by chemical structure variation. This was outstandingly successful with the lengthening of the alkyl chain by two CH$_2$ groups and the use of a cis double bond. The product is oleyl phosphocholine. Among the alkyl phosphocholine group, this is a molecule with especial and outstanding therapeutic properties. Hence according to the invention oleyl phosphocholine is particularly preferably used.

Furthermore, it was found according to the invention that compounds with an additional CH$_2$ group on the nitrogen (i.e. N,N-dimethyl-N-ethyl-ethanolamine compounds) exhibit an increase in therapeutic index compared to choline compounds. Hence, in addition to oleyl phosphocholine, oleyl phospho-(N,N-dimethyl-N-ethyl)-ethylammonium should also in particular be mentioned. The additional CH$_2$ group on the nitrogen results in an increase in therapeutic index of about 25% compared to oleyl phosphocholine.

Surprisingly, it was found that oleyl phosphocholine is already active in very small quantities and could therefore also be administered in physiological saline solution, intravenously and intramuscularly, without side effects. Formulation as liposome is not necessary. Oral and topical administration are also possible. Surprisingly, the earlier finding that alkyl phosphocholines with 16 to 20 carbon atoms cannot be used in free form as a micellar solution owing to severe side effects such as hemolysis, cytolysis and thrombophlebitis does not apply to oleyl phosphocholine. The reason for this is that in man and in dogs oleyl phosphocholine works well at very low daily dosages of for example 0.15 to 1.5 mg/kg body weight, while at these dosages hexadecyl phosphocholine remains without effect against leishmaniasis. Direct use of the free active substance is therefore possible. In particular, in the drug produced according to the invention, the active substance is not present in liposomal form.

The compounds according to the invention are already active at very low dosages. Typical dosage units are from 0.1 to 5 mg, in particular to 4 mg, in particular from 0.2 to 2 mg and still more preferably from 0.3 to 0.9 mg per kg of body weight per day. The treatment can thus be effected with extremely low quantities: daily doses of 0.1 to 0.9 mg/kg body weight suffice.

The low dosages open a broad window for new uses, in particular for long-term administration and/or continuous administration. This was previously not possible with hexadecyl phosphocholine owing to said side effects, in particular the renal toxicity.

Preferred daily doses per kilogram patient body weight (where the patient can be a person or an animal) are from 0.1 to 2 mg, in particular from 0.15 to 1.5 mg, preferably from 0.2 to 1.2 mg, more preferably from 0.3 to 0.9 mg and still more preferably from 0.5 to 0.8 mg.

Suitable pharmaceutical forms are for example normal physiological solutions, in particular physiological saline solution, tablets or aerosols.

According to the invention, the compounds of the formula (I) are preferably used for the treatment of mammals and most preferably for the treatment of dogs or people.

The active substances of the formula (I) are especially suitable for curing life-threatening diseases such as leishmaniasis and controlling severe diseases such as cancer on a long-term basis. Indeed our experience with the long-term or even continuous treatment of dogs with oleyl phosphocholine has shown that these animals benefit on a long-term basis and can reach their normal life's end in an excellent state of health.

According to the invention, compounds of the formula (I) can in particular be used for the treatment and/or prophylaxis of protozoan diseases. They exhibit outstanding activity against protozoa and diseases caused thereby. They are especially effective against plasmodia and hence are suitable for the treatment or prophylaxis of sleeping sickness, against amoebae, e.g. endamoebae and acanthamoebae, for the treatment or prophylaxis of amoebic dysentery and encephalitis and in particular against leishmaniasis. In addition to the treatment of people, according to the invention the drug preparations can also advantageously be used in the treatment of animals and in particular in leishmaniasis in dogs. Particularly preferably, according to the invention the compounds of the formula (I) are used for the treatment of leishmaniasis and/or for the treatment of diseases caused by amoebae.

Furthermore, it has been found that the compounds of the formula (I) are outstanding antitumor agents. Thus they can be used for the treatment and/or prophylaxis of cancer, in particular of leukemia and solid tumors. The substances have also thoroughly proved their worth in the treatment of cancer in dogs. Thus for example Cushin's disease and bladder tumors could be treated with good results.

In addition, they can be used for the stimulation of leukopoesis and for the treatment of diseases which are caused by arthropods and of acariosis.

Surprisingly, it has been found that the compounds of the formula (I) also exhibit good activity against acariosis, in particular mange and against diseases caused by ascarids, such as for example mites or ticks.

Further, the compounds of the formula (I) also exhibit outstanding activity against bacterial diseases. They can therefore also be used for the treatment and/or prophylaxis of bacterial diseases, in particular for the treatment and/or prophylaxis of ehrlichiosis. Ehrlichiosis is a bacterial disease which is transmitted by ticks. In the treatment of dogs, not only was a marked reduction of the ehrlichiosis titer noted, but cures were also achieved.

Eye diseases which are associated with cell proliferation, such as for example proliferative vitreoretinopathy or retinal detachment in the eye, which can only be treated with difficulty surgically, and are also often associated with very strongly proliferating cells, can also be successfully treated or avoided.

The treatment of said diseases can be effected with practically no side effects. Surprisingly, the use of the compounds of the formula (I) does not lead to the immunosuppression feared in chemotherapy, but rather even to the stimulation of leukopoiesis. With increasing duration of treatment, the blood profile also normalizes. In other words, the compounds of the formula (I) described here as active substances are very suitable for long-term treatments and make treatment without side effects possible at therapeutically effective doses.

The compounds of the formula (I) especially emphasized herein are those with at least one cis double bond in the molecule, particularly preferably oleyl phosphocholine. Alkyl phosphocholines with cis double bonds are characterized by a considerably greater therapeutic index, i.e. markedly higher doses can be administered than with saturated alkyl phosphocholines. This is especially advantageous when the therapy is combined with radiation therapy. Tumor cells doped with oleyl phosphocholine are sensitized and particularly susceptible to radiation therapy.

Surprisingly, it was found that the compounds of the formula (I) are also outstandingly suitable for treatment and/or prophylaxis in animals, in particular in dogs. Accordingly, the compounds of the formula (I) are preferably used in veterinary medicine and there in particular for the treatment of tumor and protozoan diseases. Particularly in dogs, in which previous drugs suitable for man have often failed, outstanding results could thus be achieved. Thus for example leishmaniasis and ehrlichiosis in animals and in particular in dogs can be successfully treated with the compounds of the formula (I). Particularly preferably, oleyl phosphocholine is used here as the active substance.

Further, it was found that eye diseases, in particular eye diseases associated with uncontrolled cellular processes, can be successfully treated with the compounds of the formula (I).

The compounds of the formula (I), particularly in free form (i.e. not as liposomes), are thus particularly suitable for the treatment and/or prophylaxis of cancer, of protozoan diseases such as leishmaniasis and amoebic diseases, of acariosis and of diseases which are caused by arthropods and of bacterial diseases such as for example ehrlichiosis. Eye diseases which are associated with uncontrolled cellular processes can also be favorably influenced.

The compounds of the formula (I) also have a marked action against fungal diseases, particularly against systemic fungal diseases. The compounds can therefore in addition also be used in plant protection.

The possibility of long-term or continuous treatment opens up entirely new therapeutic fields. As a result, chronic diseases such as multiple sclerosis can be continuously favorably influenced and the progression of the disease inhibited.

Further, there are also interesting possible uses in diseases which are associated with allergic reactions, just as in diseases which involve inflammatory reactions. Here, the common background is always that the compounds of the formula (I) inhibit uncontrolled cell growth, cell proliferation.

With the low toxicity compounds of the formula (I) now available, previous experience in the treatment of psoriasis can again be updated. The favorable results already achieved previously should be markedly further improved with oleyl phosphocholine.

EXAMPLES

Example 1

Below, dosage ranges are stated for hexadecyl phosphocholine and for oleyl phosphocholine, with the first number showing the start of activity and the second number the start of toxicity (see table 1). Hexadecyl phosphocholine is a registered drug, and oleyl phosphocholine is a compound of the formula (I) according to the present invention. Hence, only estimated values can initially be stated for oleyl phosphocholine use in man, and these are appropriately marked with "g" (see table 1).

TABLE 1

| HePC | (M. Wt. 407.57) |
| --- | --- |
| Rat | 20-70 μmol = 8.0-30.0 mg |
| Dog | 7 μmol = 3.0 mg |
| Man | 4-6 μmol = 1.5-2.5 mg |
| OlPC | (M. Wt. 433.61) |
| Rat | 10-150 μmol = 4.0-65.0 mg |
| Dog | 0.6-10 μmol = 0.3-4.5 mg |
| Man | 0.6-10 μmol = 0.3-4.5 mg (values estimated) |

Example 2

The production of the compounds of the formula (I) is effected analogously to the procedure described in DE 4132344 A1.

The invention claimed is:

1. A method for the treatment of protozoan diseases, bacterial diseases, cancer, multiple sclerosis, acariosis, eye diseases, fungal diseases and/or psoriasis, in a patient in need of such treatment while avoiding the concomitant liability of toxicity associated with said treatment when administering an effective dose of hexadecyl phosphocholine, comprising administering to the patient a compound of the formula (I)

$$R^1\text{—O—PO}_2^{(-)}\text{—O—}(CH_2)_2\text{—N}^{(+)}\text{—R}^2(CH_3)_2 \qquad (I)$$

wherein
R¹ is an oleyl residue and
R² is $CH_3$,
in an amount of 0.1 to 0.9 mg/kg body weight/day.

2. The method of claim 1, wherein the compound is administered in a quantity of 0.5 to 0.8 mg/kg body weight/day.

3. The method of claim 1, wherein the compound of the formula (I) is present in free, non-liposomal form.

4. The method of claim 1, wherein the compound is administered in physiological solution or in tablets.

5. The method of claim 1, wherein the compound is administered orally or subcutaneously.

6. The method of claim 1, comprising administering further active substances.

7. A method for the treatment of protozoan diseases, bacterial diseases, cancer, multiple sclerosis, acariosis, eye diseases, fungal diseases and/or psoriasis, in a patient in need of such treatment, comprising administering to the patient a compound of the formula (I)

$$R^1-O-PO_2^{(-)}-O-(CH_2)_2-N^{(+)}-R^2(CH_3)_2 \qquad (I)$$

wherein
R¹ is an oleyl residue and
R² is $CH_3$,
in an amount of 0.1 to 0.9 mg/kg body weight/day.

8. The method of claim 7, wherein the compound is administered in a quantity of 0.5 to 0.8 mg/kg body weight/day.

9. The method of claim 7, wherein the compound of the formula (I) is present in free, non-liposomal form.

10. The method of claim 7, wherein the compound is administered in physiological solution or in tablets.

11. The method of claim 7, wherein the compound is administered orally or subcutaneously.

12. The method of claim 7, comprising administering further active substances.

* * * * *